United States Patent [19]
Hatton et al.

[11] Patent Number: 5,315,117
[45] Date of Patent: May 24, 1994

[54] VOLUME METER SYSTEM

[75] Inventors: Gregory J. Hatton; David A. Helms; Michael G. Durrett, all of Houston, Tex.

[73] Assignee: Texaco Inc., White Plains, N.Y.

[21] Appl. No.: 26,356

[22] Filed: Mar. 4, 1993

[51] Int. Cl.$^5$ .............................................. G01F 23/22
[52] U.S. Cl. ................................ 250/356.1; 250/357.1
[58] Field of Search ................ 250/357.1, 356.1, 356.2

[56] References Cited
U.S. PATENT DOCUMENTS 4,282,433  8/1981  Löffel ................................ 250/356.1
5,025,160  6/1991  Watt .................................. 250/356.1

*Primary Examiner*—Constantine Hannaher
*Attorney, Agent, or Firm*—George J. Darsa; Ronald G. Gillespie; Russell J. Egan

[57] ABSTRACT

A system determines the relative amounts of phases in multiphase flow, typically the liquid (or gas) fraction of a stream in two-phase flow. More particularly, the system quickly and reliably determines the liquid (or gas) fraction of a flowing two-phase stream, such as a process stream commonly found in chemical processing or in petroleum production operations. The system yields accurate results regardless of the exact flow regime under which the two-phase stream is flowing.

8 Claims, 5 Drawing Sheets

VOLUME METER SYSTEM

BACKGROUND OF THE INVENTION

1. Field of the Invention

The present invention relates to determining the relative amounts of phases in multiphase flow, typically the liquid (or gas) fraction of a stream in two-phase flow. More particularly, the present invention relates to quickly and reliably determining the liquid (or gas) fraction of a flowing two-phase stream, such as a process stream commonly found in chemical processing or in petroleum production operations. The present invention yields accurate results regardless of the exact flow regime under which the two-phase stream is flowing.

2. Description of the Prior Art

It is often important to have a reliable on-line quantitative measurement of the relative amounts of the various phases present in a stream containing multiple phases. Such streams are often encountered in the context of a petroleum refinery, a chemical plant, or in the production of petroleum from underground reservoirs. Many such streams typically contain multiple phases. A measurement of the relative amounts of the various phases is not only important in determining the amounts of liquid and gas in a custody transfer context, but is also often crucial in the context of chemical process operations in allowing the operators and/or the automatic control equipment to adjust process parameters so as to optimize the operation and avoid unprofitable and/or dangerous operating conditions.

Various attempts have been made to determine the relative amounts of the various phases in multiphase flow. The best methods have been found to be those involving radiation attenuation techniques. For this purpose, gamma rays or x-rays have been often used.

Generally, radiation attenuation techniques involve the irradiation of a small section of the pipe through which the stream to be measured is flowing. The radiation enters the pipe by passing through the pipe wall on the side closer to the radiation source. The radiation then passes through the fluid in the pipe. Finally, the radiation exits the pipe by passing through the pipe wall on the side away from the radiation source.

As the radiation passes through the various materials, some of the radiation is absorbed and de-energized. Thus, as the stream of radiation passes through the various substances in its path, the amount of radiation continuing on a straight path from the source is decreased, or attenuated. The degree of attenuation depends on the properties of the materials through which the radiation passes and on the amounts of those materials present in the path of the radiation beam. The amount of radiation surviving its passage through the various materials in its path is then detected by appropriate radiation detectors.

An advantage of the radiation attenuation method is that the apparatus can be mounted completely outside the pipe and thus does not in any way interfere with the stream being analyzed.

Of great interest in the measurement of multiphase streams is the instantaneous liquid (or gas) fraction across the pipe. It is known to use an apparatus for determining the liquid (or gas) fraction which uses a radiation source to direct a single beam of radiation at a pipe, and to detect the attenuated radiation beam exiting the pipe. However, it is well known that the liquid (or gas) is not homogeneously distributed across the pipe cross-section. Thus, use of a single beam apparatus can lead to large errors in the determination of the overall liquid (or gas) fraction.

A number of solutions have been attempted in an effort to overcome this problem. One such solution is to cause the single radiation beam to traverse the entire pipe cross section and to take an appropriate weighted average of the attenuated beam in determining the average liquid (or gas) fraction. This technique suffers from at least two shortcomings. First, the method requires movement of the radiation beam which introduces considerable mechanical complexities to the system and reduces system reliability and ruggedness. Second, since a certain finite time is required for the radiation beam to traverse the entire pipe cross section, the average liquid (or gas) fraction calculated reflects the average fraction over a certain small but finite period of time, rather than an instantaneous real-time reading of the liquid (or gas) fraction.

To overcome the difficulties associated with single radiation beam techniques, work has been done to develop a one-shot-collimator measurement, also known as the wide beam measurement. The wide beam technique calls for the simultaneous bombardment of the entire cross-section of the pipe with a beam of radiation emanating from a single source, and for the simultaneous detection of the attenuated radiation exiting the pipe. This arrangement provides an instantaneous response which is representative of the average liquid (or gas) fraction of the stream in the pipe. The average reading is obtained by summing the attenuations of the various portions of the radiation beam. Such a technique is described, for example, in "On the Gamma-Ray One-Shot-Collimator Measurement of Two-Phase-Flow Void Fractions", R. P. Gardner, R. H. Bean, and J. K. Ferrell, Nuclear Applications & Technology, Vol. 8, January 1970, pp. 88-94.

While the wide beam technique described above is capable of yielding accurate measurements for two-phase flows wherein the two phases are intimately mixed, large errors are obtained when the technique is used to determine liquid (or gas) fractions in two-phase systems wherein the two phases are relatively distinct and separate from one another, such as is the case where, for example, the phases are in annular flow with gas flowing through the central region of the pipe with the liquid flowing in an annular area near the pipe walls, or in stratified flow, where the liquid tends to concentrate near the bottom portion of the horizontal or inclined pipe while the gas tends to locate toward the upper portions of the pipe cross section.

SUMMARY OF THE INVENTION

Apparatus determines relative volumes of phases in a multiphase fluid flowing in a pipe under any one of a number of commonly encountered flow regimes. A radiation source emits radiation beams which are collimated by a collimator and directed towards the pipe. An attenuator attenuates the beams from the collimator, said attenuator has a shape optimized to compensate for the pipe geometry and for possible existence of any one of the aforementioned flow regimes. A detector, positioned so that the pipe is between the detector and the attenuator, senses gamma radiation.

The objects and advantages of the present invention will appear more fully hereinafter from a consideration of the detailed description which follows, taken together with the accompanying drawings wherein one embodiment of the invention is illustrated by way of example. It is to be expressly understood, however, that the drawings are for illustration purposes only and not to be construed as defining the limits of the invention.

DESCRIPTION OF THE INVENTION

Figure 1:
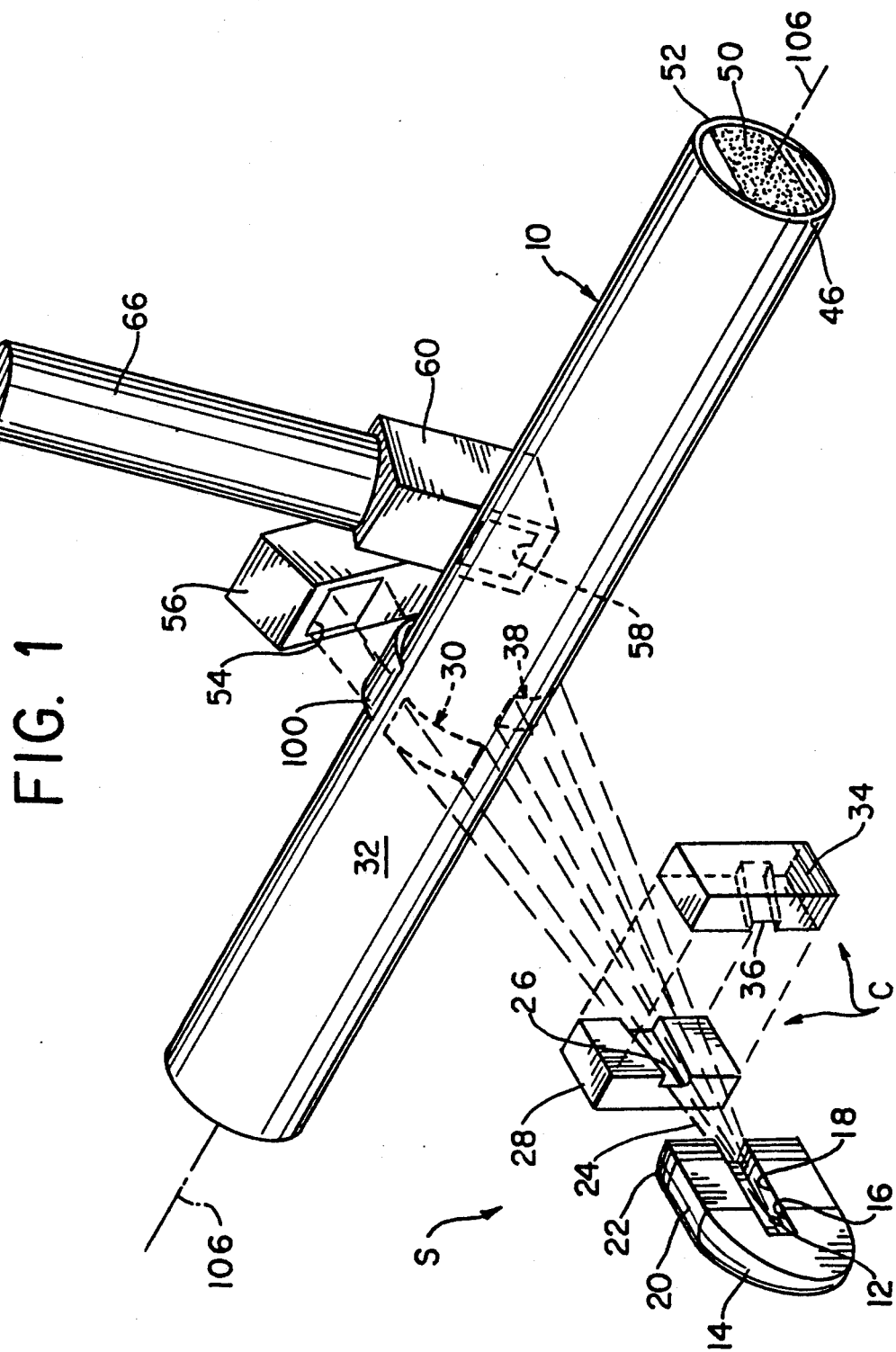
FIG. 1 is an isometric view, partially exploded, of an apparatus according to the present invention.

In the drawings, a volume meter system S according to the present invention for determining the relative amounts of phases in multiphase flow is shown. A multiphase stream, typically a two phase stream containing liquid and gas, flows through a pipe 10 in a petroleum gathering, distribution or processing operation. Pipe 10 may be made of any typical suitable pipe material used in petroleum operations, such as steel or the like. Pipe 10 can be vertically or horizontally oriented, depending on the location in the petroleum operation where it is desired to determine the relative amounts of phases in multiphase flow. In some situations, the pipe 10 may also be in an inclined position.

A volume meter system S according to the present invention provides fast, accurate readings of the volume fractions of fluids in pipe 10. The meter system S includes a radiation source 12 of high energy neutrons. Radiation source 12 is preferably located in a plane which is transverse to the longitudinal axis of fluid flow within pipe 10. Radiation source 12 is preferably a continuous gamma source, such as one formed of $^{137}$Cs, emitting gamma rays which bombard the pipe 10, its contents and their surrounds. Other continuous sources of high energy gamma rays might also be used, if desired. A neutron or pulsed neutron source might also be used as source 12.

Radiation source 12 is located within a hemispherical radiation shield 14, typically from a highly absorbing material such as lead. An opening 16 in radiation shield 14 allows radiation emitted from source 12 to pass into a passage 18 formed in a cylindrical shield 20 in the desired direction toward pipe 10. The shield 20 may include additional thickener plates or disks 22, as indicated.

Radiation from source 12 emerging from shield 20 is thus in the form of a relatively narrow beam, as indicated at 24, which passes into an opening 26 in a first or upper radiation collimator section 28 of a collimator C. Upper collimator 28 serves to allow passage of only those gamma rays in beam 24 which impinge on an area 30 of an external arcutate upper half-surface 32 of pipe 10.

A second or lower radiation collimator section 34 of collimator C has an opening 36 formed therein which allows passage of only those gamma rays in beam 24 which impinge on an area 38 of an external lower arcuate half-surface 40 of pipe 10. The upper and lower collimator sections 28 and 34 of collimator C are shown separated from each other in FIG. 1 in order that their structure may be more clearly seen.

Figure 2:
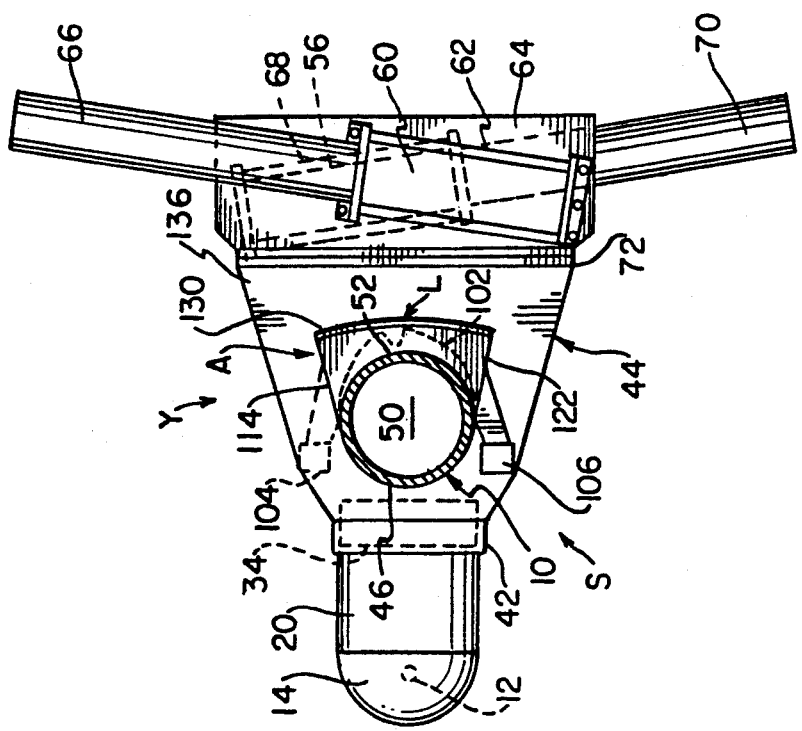
FIG. 2 is an elevation view, taken partly in cross-section, of the apparatus of FIG. 1.
Figure 4:
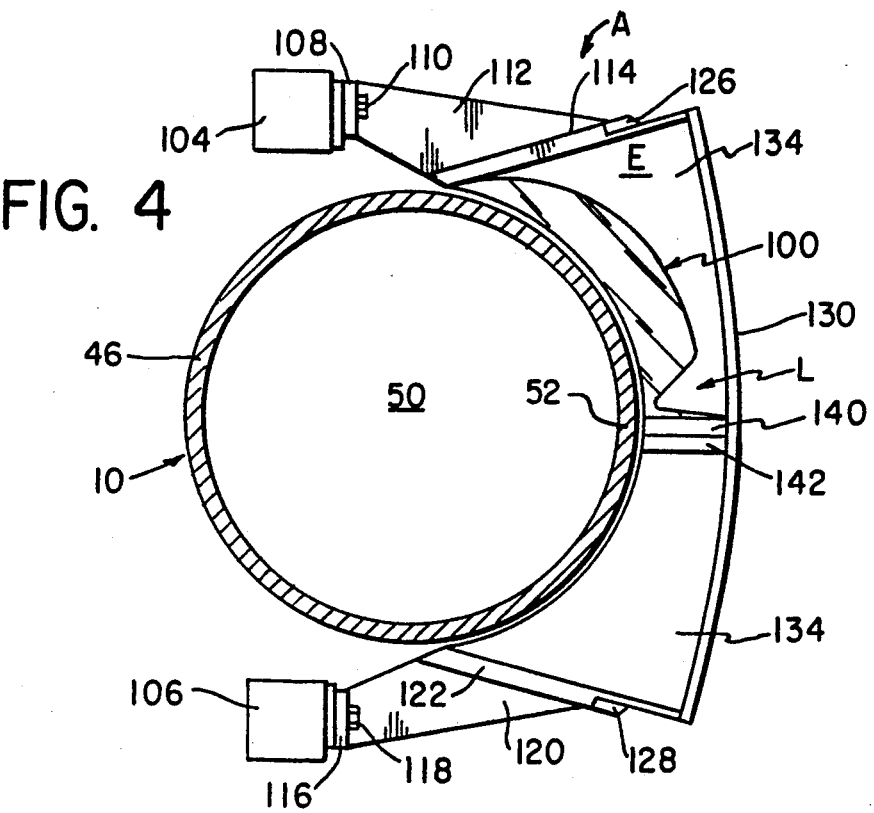
FIG. 4 is a view taken along the lines 4—4 of FIG. 3.
Figure 5:
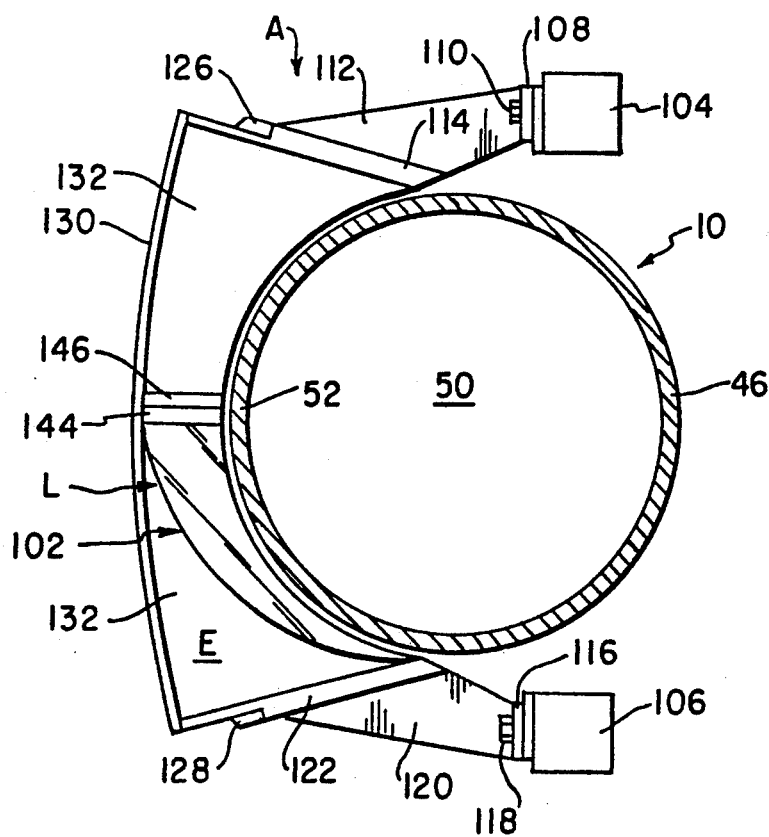
FIG. 5 is a view taken along the lines 5—5 of FIG. 3.

Radiation shield 14 containing source 12 and shield 20 are mounted with collimator C and 34 by a mounting collar 42 (FIG. 2) of the system S. The collimator C is connected by a mounting connector mechanism 44 of a mounting yoke Y which serves to attach the system S to pipe 10 at the desired location. Mounting collar 42 and connector mechanism 44 are shown in FIG. 1 in order that the collimators and certain other portions of the system S functioning to direct radiation from the source 12 onto pipe 10 may be more clearly seen.

Radiation from source 12 enters pipe 10 at arcuate surface portions 32 and 40, travelling in radially outwardly expanding paths (FIG. 1) from the point source 12. The radiation travels first through a first or closer wall 46 of the pipe 10 nearer the source 12. Radiation entering wall 46 (FIG. 6) of pipe 10, depending on its point of entry, passes through through a certain thickness of pipe wall 46 into fluids in interior 50 of pipe 10 and then through a second or outer wall 52 of pipe 10 further from source 12.

During the course of travel, certain of the radiation beam is attenuated. The intensity of gamma radiation is sensed at a rectilinear or planar upper window 54 (FIG. 1) of an upper gamma radiation sensor detector 56 and at a rectilinear or planar window 58 of a lower gamma radiation sensor/detector 60. Based on the amount and intensity of gamma radiation sensed in the sensors 56 and 60, the nature of flow in the pipe 10 is indicated.

The lower gamma radiation detector 60 is mounted in a bracket 62 (FIG. 2) attached to a vertically extending separator plate 64. Separator plate 64 may be formed of a radiation absorptive material, if desired, to prevent stray radiation intended for one of gamma radiation detectors 56 and 60 from being detected by the other detector. Conventional gamma radiation detector electronics including pulse height analyzers, amplifiers and the like are contained in an electronics housing 66 mounted extending above bracket 62.

The upper gamma radiation detector 56 is mounted in a bracket 68 attached to an opposite side of separator plate 64 from bracket 62. Gamma radiation detector electronic circuitry, again of the conventional type like those in housing 66, is mounted in an electronics housing 70 mounted extending downwardly from bracket 68. Brackets 62 and 68 and the separator plate 64 are mounted to a frame member 72 (FIG. 2) mounted extending transversely to the connector mechanism 44 of yoke Y.

Figure 7:
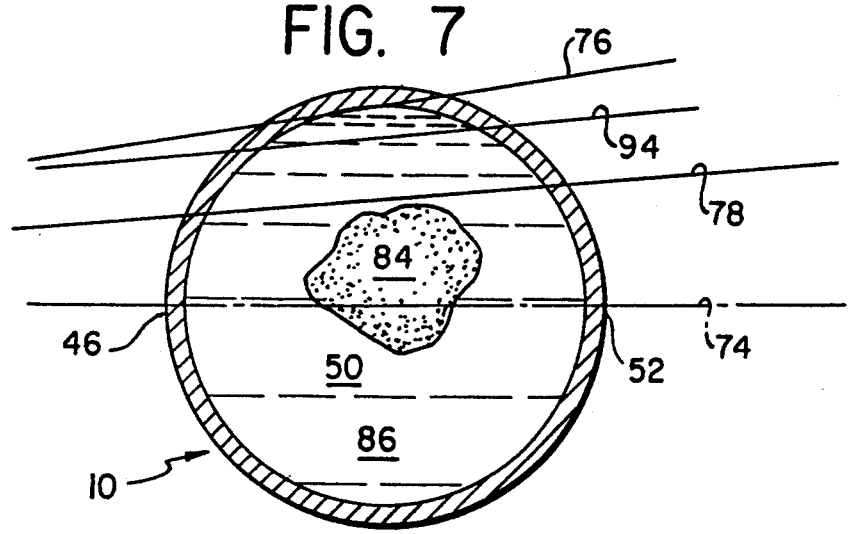

Depending on the point of entry into pipe 10, the distances travelled by radiation and the materials through which the radiation travels may vary a great deal. Consider, for example, radiation travel paths or chords shown schematically at 74, 76 and 78 (FIG. 7).

Travel path 74 intersects pipe 10 near its central axis, travel path 76 intersects pipe 10 at an upper portion, while travel path 78 intersects pipe 10 between paths 74 and 76. Inspection reveals that radiation moving along path 74 has comparatively less travel through the material of pipe 10 and comparatively high travel lengths through interior 50 of pipe 10. In contrast, radiation moving along path 76 travels entirely through the material of pipe 10, comparatively more than path 74, with no passage into interior 50 of pipe 10. Between these comparative travel paths, radiation along travel path 78 passes through intermediate amounts of material of pipe 10 and contents in interior 50 different from those on travel paths 74 and 76.

The Gardner et al. article from Nuclear Applications & Technology, referred to above, teaches techniques for compensation of the effects of differing lengths of radiation travel paths on radiation measurements. Further, the Gardner et al. article teaches compensation techniques for arrival gamma radiation at a rectilinear or planar gamma ray detector surface after travel of radiation from a point source on radially outwardly expanding travel paths. However, so far as is known, prior to the present invention no recognition has been made of the effect of fluid flow conditions in interior 50 of pipe 10 on radiation measurement.

Figure 6:
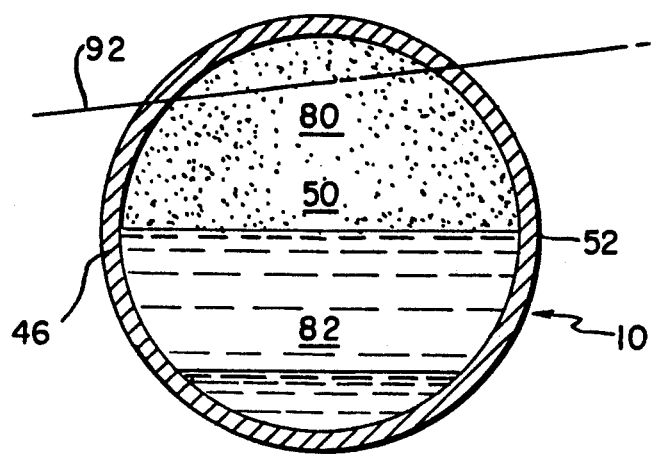
FIGS. 6, 7, and 8 are vertical cross-sectional views of various flow regimes of a two-phase (liquid/gas) mixture in a pipe.
Figure 8:
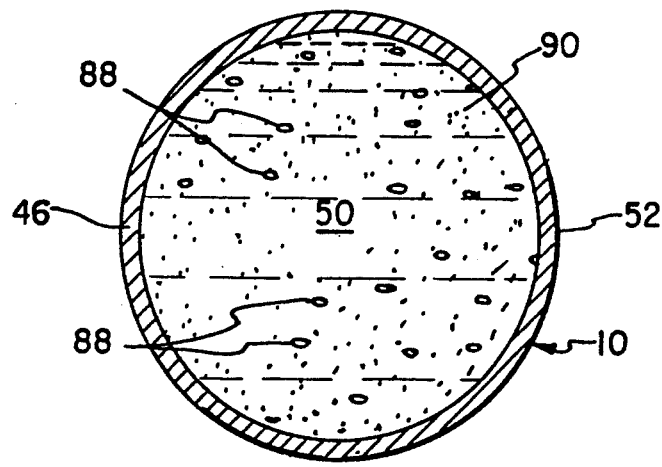

For stratified flow (FIGS. 1 and 6), a gas or mixture of gases 80 flows in pipe 10 as a stratum above one or more flowing layers of liquid 82 (FIG. 6). In annular flow (FIG. 7), a gas or gas mixture 84 flows in pipe 10 within an outer annulus of flowing liquid 86. In homogenous flow (FIG. 8), a gas or gas mixture is present as homogeneously distributed bubbles or gas pockets 88 within a liquid 90 in the interior 50 of pipe 10. Applicants have found that the type and nature of fluid flow in pipe 10 can cause different radiation measurements, even though the same void fraction of gas is present in the fluid flowing in pipe 10.

For example, radiation path 92 in stratified flow (FIG. 6) passes through only gases in the interior 50 of pipe 10. By contrast, the same radiation path 94 for annular flow (FIG. 7) passes only through liquid 86 in the interior of pipe 10. The denser liquid will attenuate radiation beam more in annular flow than the gases in stratified flow, even though identical void fractions are present for both flow situations.

Figure 9:
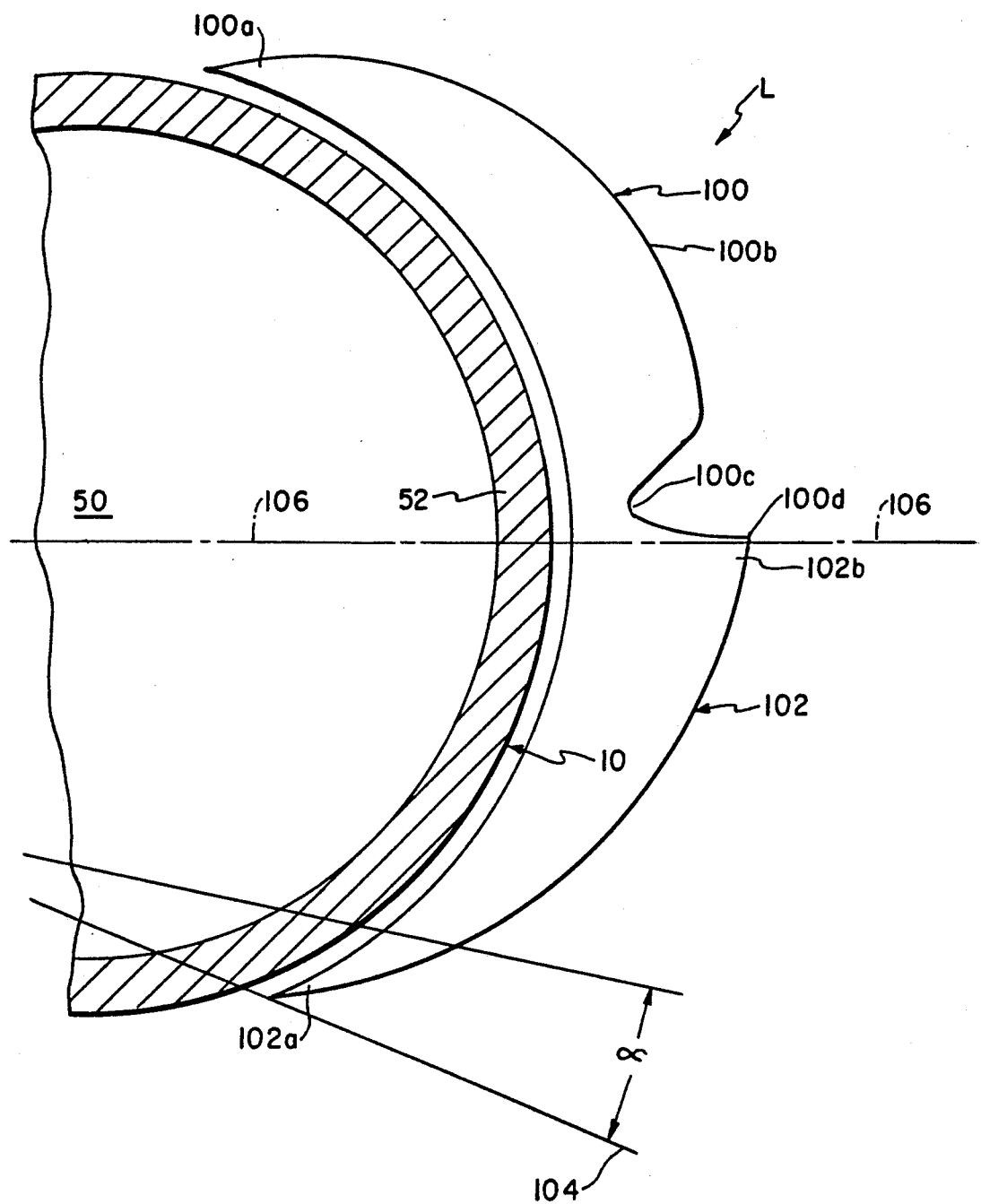
FIG. 9 is an elevation view of a radiation attenuator portion of the apparatus of FIG. 1.

With the present invention, applicants have found and developed an attenuator/lens pair L (FIG. 9) for interposition between radiation source 12 and gamma ray detectors 56 and 60. Lens system L includes an upper lens 100 mounted on an upper half of pipe 10 opposite the upper surface portion 32 and a lower lens 102 mounted on a lower half of pipe 10 opposite lower surface portion 40.

Lenses 100 and 102 of lens pair L of the system S have vertical cross-sections (FIG. 9) whose shape, as defined in a manner set forth below, not only compensates for different travel thicknesses through the walls of pipe 10, but also adjusts flux densities so that gamma radiation count rates are not affected by the type of flow in the pipe 10. For the same void fraction flowing in the pipe 10, gamma radiation count rates in the system S for homogenous, stratified or annular flow are within acceptable statistical error limits of each other.

Lower lens 102 (FIG. 9) has a thickness in vertical cross-section (FIG. 9) tapering from a thinnest lower portion 102a to a thickest upper portion 102b. The thickness of lower lens 102 can be expressed as a constant k times the radians (or fractions thereof) in a radial angle α between a beginning radiation travel path 104 which passes only through the walls of pipe 10 to a lowermost starting point of lower portion 102a. Since stratified flow does not cause anything other than fluid to be present in the lower half of pipe 10, lower lens 102 is therefore of a constantly increasing thickness from lower portion 102a to upper portion 102b at the center line of pipe 10, where a radiation travel path 106 is through minimum thickness of the wall of pipe 10 and maximum distance through the interior 50 of the pipe 10.

The upper lens 100 is of a somewhat more complex shape vertical cross-section (FIG. 9) than the lower lens 102. The thickness of upper lens 100 tapers from a thinnest upper portion 100a to a thickest intermediate portion 100b, a relatively thin inset or neck portion 100c and then again to a thicker lower portion 100d, adjacent the center portion of pipe 10, of like thickness to upper portion 102b of lower lens 102.

The lenses 100 and 102 are mounted within a lens cover assembly A (FIGS. 2-5) mounted with connector mechanism 44 of yoke Y. An upper mounting connector 104 and a lower mounting connector 106 on each side of the lens cover assembly C are bolted or otherwise suitably fastened to connector mechanism 44 of yoke Y.

The upper mounting connector 104 (FIG. 2) is attached to a transversely extending upper mounting plate 108 (FIGS. 3-5) of lens cover assembly C by bolts 110 or other suitable fasteners. An upper connector arm 112 extends from upper mounting plate 108 to a top cover portion 114 of cover C.

The lower mounting connector 106 (FIG. 2) is attached to a transversely extending lower mounting plate 116 (FIGS. 3-5) by bolts 118 or other suitable fasteners. A lower connector arm 120 extends from lower mounting plate 116 to a lower cover 122 of cover C.

Top cover 114 is mounted on upper connector arm 112 by a top cover retainer 126 (FIGS. 4 and 5) which is bolted or otherwise held mounted in place. In a like manner, lower cover 122 is held in place on lower connector arm 120 by a lower cover retainer 128 bolted or otherwise suitably fastened.

Figure 3:
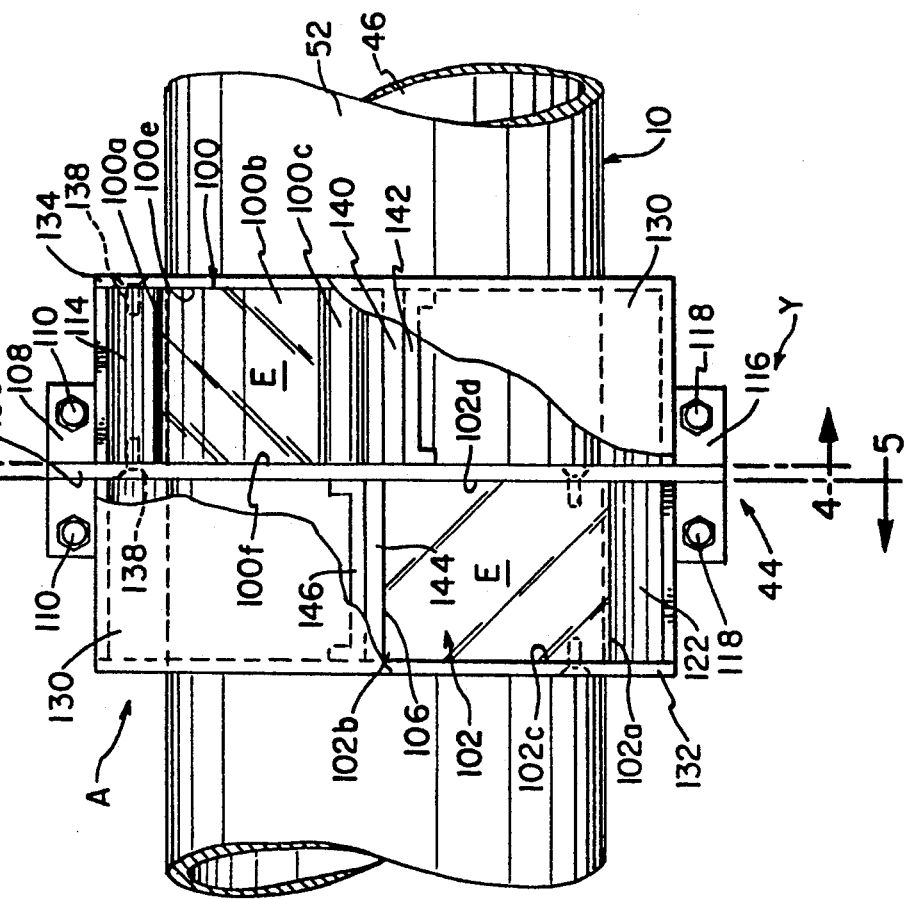
FIG. 3 is an elevation view of the apparatus of FIG. 1.

Top cover 114 and lower cover 124, together with an arcuate rear cover 130 and side cover walls 132 and 134, form an enclosed chamber E within which lens assembly L is mounted. In FIG. 3, portions of the rear cover 130 have been removed in order that mounting structure for lens assembly L in enclosed chamber E may be more clearly seen.

Upper lens 100 is mounted on side surfaces 100e and 100f (FIG. 3) between the side wall 134 and a center plate 136. Bolts 138 passing through wall 134 and center plate 136 into upper lens 100 may, for example, perform this function.

A radiation absorptive block 140, of lead or orther suitable material, is mounted below the lens 100 and above a pressure bar 142. The block 140 prevents stray radiation passing through lower portions of pipe 10 from being passed to detector 54. Block 140 is bolted or otherwise mounted to pressure bar 142, while pressure bar 142 is mounted to the side wall 134 and center plate 136 in a like manner to the lens 100.

Lower lens 102 is mounted along side surfaces 102c and 102d (FIG. 3) between side wall 132 and center plate 136 in a like manner to upper lens 100. A radiation adsorptive block 144, of lead or other suitable material, is mounted above the lens 102 and below a pressure bar 146. In a similar manner to block 140, block 144 shields detector 58 from radiation passing through upper portions of pipe 10. Block 144 is bolted or otherwise mounted to pressure bar 146. Pressure bar 146 is in turn mounted to side wall 132 and center plate 136 in a like manner to lenses 100 and 102.

The vertical cross-section shapes of the lenses L are based on average radiation attenuation needed under a variety of flow conditions within the pipe 10 to provide substantially the same radiation counts for the same void fractions.

The system S can be considered for each of the detectors 54 and 58 as composed of a number n of radiation beams travelling on radiation paths or chords, each leading to a detector. The neutron flux F for a given fluid distribution (fd) within the pipe 10 can be expressed as a product $F_{red}$ of matrix multiplication of A and I as follows:

$$F_{red} A \cdot I \qquad (1)$$

where $F_{red}$ is vector of radiation fluxes for different fluid distribution, A is flux attenuation matrix and I is a tensor of incident fluxes.

For example, one desirable condition to impose in determination of I is that $F_{red}$ be the same for a homogenous gas/fluid mixture having a void fraction of 0.2 as for a stratified gas/fluid distribution having the same void fraction. Expressed mathematically, $$O = F_{red}(.2 \text{ void homog}) - F_{red}(.2 \text{ void strat})$$

For a system of n beams, the vector I thus has n elements. Consequently, n−1 conditions may be specified. This leads to a matrix equation of the form $$O = A\_A \cdot I$$

where I is of dimension n, and A_A is of dimension n−1 by n, and $$A\_A(j,i) = A(fd,1) - A(fd',i)$$

where j is the condition index, and fd and fd' are fluid distributions having the same cross-sectional average attenuation but different flow patterns. Matrix Equation (4) can be readily solved in a computer using conventional computer matrix computations to determine a matrix I which when multiplied by a matrix F of fluid attenuators for various flow conditions minimizes (in an optimum situation, reduces to zero) the matrix product.

Computations to determine lens shape for lens L in the foregoing manner can be done for a variety of liquid fractions and for any one or more of the following distributions:

(a) homogenous (gas and liquid homogeneously distributed);
(b) stratified (gas stratified above liquid);
c) stratified/bubble (gas stratified above a homogenous liquid/gas mixture, the total gas is the gas in the homogenous mixture and the gas stratified above the mixture);
(d) annular (gas inside a circle inside and concentric to the pipe and a homogenous liquid/gas mixture outside this circle); and
(e) annular/droplet (gas/liquid mixture inside a circle and concentric to the pipe and a homogenous liquid/gas mixture outside this circle).

Stratified calculations are carried out only for horizontal and inclined configurations. Gas/liquid mixtures are homogenous mixtures with a gas fraction $\geq 0.5$. Liquid/gas mixtures are homogenous mixtures with a gas fraction $\geq 0.5$. At the lens designer's discretion, these gas fractions may be fixed or varied during the calculation. More complicated mixtures—for example, a liquid/gas mixture in which the local gas fraction varies with some geometrical parameter such as height—may also be used. The inside circle need not be concentric, but in general the center of the inside circle and the pipe lie on the line which is the intersection of the normal plane to the pipe and the vertical plane containing the center line of the pipe.

By requiring that the flux count rate $F_{red}$ be the same for two such distributions for a number of liquid fractions likely to be encountered in expected conditions in the pipe 10. In the embodiment described, the lens system L is on the pipe 10 opposite the radiation source 12. It should be understood that the lens system L may be mounted between the pipe 10 and the radiation source 12, if desired.

In operation, the present invention permits real-time analyses of the phase fractions of a flowing two-phase stream in a convenient section of pipe 10. The system S is activated by energizing the radiation detectors 54 and 58 and their electronics. The measurements obtained are then used to calculate the average instantaneous liquid (or gas) fraction of the stream in the pipe 10. Because of the designed configuration of the lens L, the calculated liquid (or gas) fraction is accurate within a small error regardless of the type of flow regime under which the two-phase stream is flowing.

Having described the invention above, various modifications of the techniques, procedures, material and equipment will be apparent to those in the art. It is intended that all such variations within the scope and spirit of the appended claims be embraced thereby.

What is claimed is:

1. An apparatus for determining relative volumes of phases in a multiphase fluid flow under any one of a number of commonly encountered flow regimes through a pipe, comprising:
   (a) a radiation source located outside the pipe capable of emitting radiation beams toward and through the pipe;
   (b) collimating means for collimating the radiation beams toward the pipe;
   (c) attenuation means located in the path of the radiation beams and having a shape optimized to compensate for the pipe geometry and for the possible existence of any one of a number of commonly encountered flow regimes in the pipe;
   (d) detecting means located on the pipe opposite the radiation source for sensing the gamma radiation.

2. An apparatus as in claim 1 wherein the flow is a two-phase flow.

3. An apparatus as in claim 1 wherein the flow is a two-phase flow including a liquid phase and a gas phase.

4. An apparatus as in claim 1 further comprising a radiation shield for shielding said source.

5. An apparatus as in claim 1 wherein said collimating means is a collimator.

6. An apparatus as in claim 1 wherein said attenuation means includes a shaped attenuator located between said radiation source and the pipe.

7. An apparatus as in claim 1 wherein said attenuation means includes a shaped attenuator located between the pipe and said detecting means.

8. An apparatus as in claim 1 wherein said detecting means includes a pair of linear radiation detectors, each of said detectors capable of detecting gamma radiation exiting from substantially different halves of the pipe cross section.

* * * * *